United States Patent [19]

Shroot et al.

[11] Patent Number: 4,696,941
[45] Date of Patent: Sep. 29, 1987

[54] 1,8-DIACYLOXY-10-ACYLANTHRONES

[75] Inventors: Braham Shroot, Antibes; Gérard Lang, Epinay-sur-Seine; Jean Maignan, Tremblay les Gonesse, all of France

[73] Assignee: Groupement d'Interet Economique dit: Centre International 'de Recherches Dermatologiques C.I.R.D., Valbonne, France

[21] Appl. No.: 750,088

[22] Filed: Jun. 28, 1985

[30] Foreign Application Priority Data

Jun. 29, 1984 [FR] France .................. 84 10324

[51] Int. Cl.⁴ ............ A01N 35/00; C07C 50/70; C07C 50/16
[52] U.S. Cl. ............ 514/423; 260/351; 548/571; 548/572; 548/573; 549/78; 549/79; 549/498; 549/499; 514/448; 514/461; 514/676; 514/680; 514/852; 514/859; 514/861; 514/863; 514/882
[58] Field of Search ............... 260/351; 514/510, 882, 514/423, 448, 461, 676, 680, 852, 859, 861, 863; 548/571, 572, 573; 549/78, 79, 498, 499

[56] References Cited

U.S. PATENT DOCUMENTS 4,007,271 2/1977 Robertson .................. 260/351
4,299,846 11/1981 Mustakallio et al. ......... 260/351

FOREIGN PATENT DOCUMENTS 0017420 10/1980 European Pat. Off. ....... 260/351
2140007 11/1984 United Kingdom ........... 260/351

OTHER PUBLICATIONS

Chemical Abstracts, vol. 81, No. 13, 30 Sep. 1974, p. 443, No. 77722s, P. Hofer et al.

Chemical Abstracts, vol. 88, No. 15, 10 Apr. 1978, p. 538, No. 104986j, O. E. Schultz et al.

French Search Report for Application 84-10,324.

*Primary Examiner*—Glennon H. Hollrah
*Assistant Examiner*—Raymond Covington
*Attorney, Agent, or Firm*—Wegner & Bretschneider

[57] ABSTRACT

Compounds of the formula

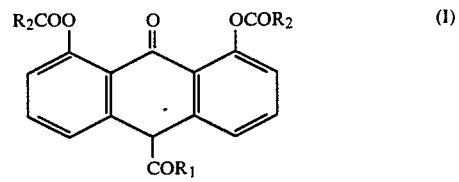

wherein $R_1$ and $R_2$ are the same or different and represent a straight-chain or branched alkyl group of 1 to 15 carbon atoms, a cycloalkyl group of 3 to 6 carbon atoms, a 2-furyl, 3-furyl, 3-pyridyl, 4-pyridyl or 2-thienyl group or an aromatic group of the formula

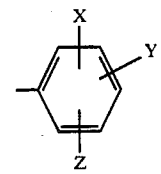

wherein X, Y and Z are the same or different and represent hydrogen, alkyl of 1 to 3 carbon atoms, trifluoromethyl, alkoxy with 1 to 4 carbon atoms, halogen, nitro or hydroxy groups are useful as pharmaceutical, veterinary and cosmetic agents.

8 Claims, No Drawings

1,8-DIACYLOXY-10-ACYLANTHRONES

The present invention relates to novel compounds, the 1,8-diacyloxy-10-acylanthrones, which are derivatives of 1,8-dihydroxyanthrone or anthralin, processes for preparing these compounds and the use of these compounds in human or veterinary medicine and in cosmetics. In human or veterinary therapeutics, these compounds are anti-proliferative agents, particularly in the treatment of psoriasis and warts, or anti-inflammatory agents in the treatment of rheumatic diseases, dermatoses and eczema. In cosmetics, these compounds are anti-acne, anti-dandruff, anti-seborrhea and anti-hair-loss agents.

Compared with anthralin and some of its derivatives such as those described in U.S. Pat. No. 4,299,846, the 1,8-diacyloxy-10-acylanthrones have the advantage of being less irritating and more stable, and of not staining the skin and the clothes, particularly in washing with basic fluids.

Moreover, compared with the compounds described in German Pat. No. 2,154,609, the 1,8-diacyloxy-10-acylanthrones have much greater stability in time.

The 1,8-diacyloxy-10-acylanthrones of the invention can be represented by the general formula

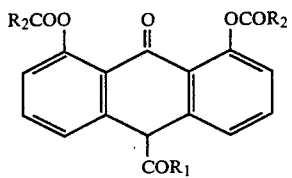

wherein:

$R_1$ and $R_2$, which may be identical to or different from each other, are each a linear or branched alkyl group with 1 to 15 carbon atoms, a cycloalkyl group with 3 to 6 carbon atoms, a 2-furyl or 3-furyl group, a 3-pyridyl or 4-pyridyl group, a 2-thienyl group or an aromatic group of the formula

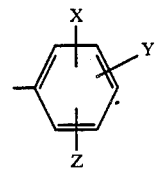

wherein:

X, Y and Z, which may be indentical to or different from each other, are each hydrogen, an alkyl group with 1 to 3 carbon atoms, a trifluoromethyl group, an alkoxy group having 1 to 4 carbon atoms, a halogen, a nitro group or a hydroxyl group.

When $R_1$ and $R_2$ represent an alkyl group, this is preferably a methyl, ethyl, propyl, isopropyl, butyl, isobutyl, tert-butyl, pentyl, isopentyl, heptyl, nonyl, undecyl or pentadecyl group.

When $R_1$ and $R_2$ represent a cycloalkyl group, this is preferably a cyclopentyl or cyclohexyl group.

When $R_1$ and $R_2$ represent an aromatic group, this is preferably a phenyl group or a monosubstituted or di-substituted phenyl group.

X, Y and Z preferably represent a lower alkyl group such as methyl, ethyl, or tert-butyl, an alkoxy group such as methoxy or ethoxy or a halogen atom such as a chlorine or fluorine atom.

Of the compounds of formula (I), the following in particular can be mentioned:
1,8-diacetoxy-10-acetylanthrone,
1,8-diacetoxy-10-propionylanthrone,
1,8-dipropionyloxy-10-propionylanthrone,
1,8-diisobutyryloxy-10-propionylanthrone,
1,8-diacetoxy-10-isobutyrylanthrone,
1,8-dipropionyloxy-10-isobutyrylanthrone,
1,8-diisobutyryloxy-10-isobutyrylanthrone,
1,8-dipivaloyloxy-10-pivaloylanthrone,
1,8-dipivaloyloxy-10-propionylanthrone,
1,8-diacetoxy-10-isopentanoylanthrone,
1,8-dipropionyloxy-10-isopentanoylanthrone,
1,8-diisopentanoyloxy-10-isopentanoylanthrone,
1,8-dicyclohexylcarbonyloxy-10-cyclohexylcarbonylanthrone,
1,8-diacetoxy-10-cyclopentylcarbonylanthrone,
1,8-diacetoxy-10-cyclohexylcarbonylanthrone,
1,8-dipivaloyloxy-10-benzoylanthrone,
1,8-dipivaloyloxy-10-(2'-thenoyl)-anthrone,
1,8-dipivaloyloxy-10-butyrylanthrone, The present invention also relates to processes for preparing 1,8-diacyloxy-10-acylanthrones of the above formula (I).

Access to compounds of formula (I) can be envisioned by two different synthesis routes, which can be represented by means of the following two reaction schemes (A) and (B):

Scheme A

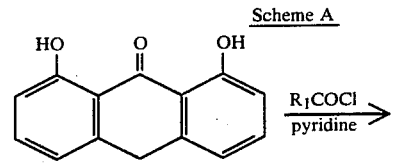

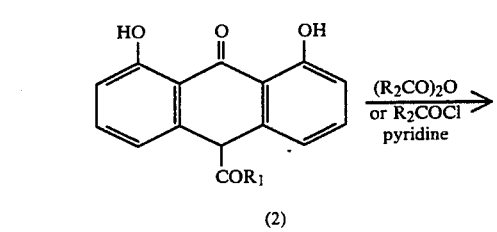

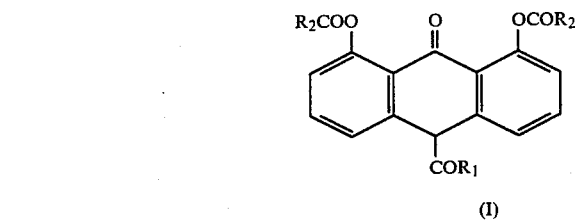

Scheme B

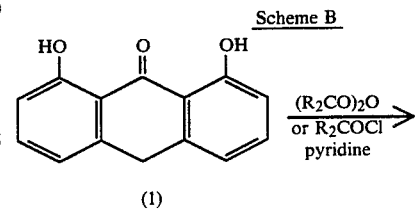

-continued
Scheme B

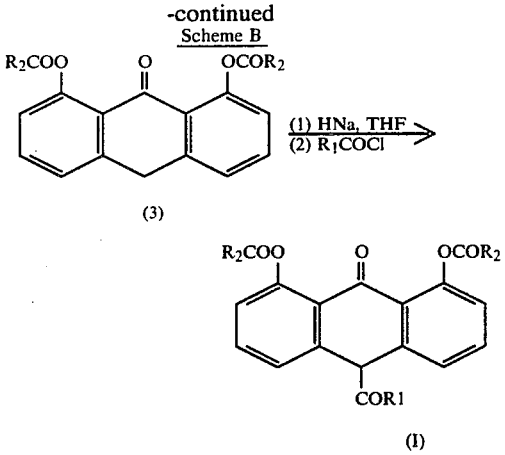

(3)

(1)

The first synthesis route (scheme A) is used preferably for preparation of compounds of formula (I) in which the acyl group at the 10-position contains a hydrogen atom in α-position with respect to the carbonyl group.

It is supposed that, by reacting an acid chloride containing a hydrogen atom in α-position with respect to the carbonyl group, an intermediate ketene is formed and then reacts with the 1,8-dihydroxyanthrone to form an adduct which is then transformed to the 10-acyl derivative of formula (2).

The second synthesis route is used more particularly for preparation of compounds of formula (I) in which the $R_2$ groups are severely hindered and more particularly when the $R_2$ groups do not contain a hydrogen atom in α-position with respect to the carbonyl group.

In the presence of a strong base, the carbanion formed at the 10-position is in equilibrium with the enol form of the carbonyl group at the 9-position and, because of the steric hindrance at the 1- and 8-positions of the compounds of formula (3), the carbanion at the 10-position is acylated preferentially by means of an acid chloride $R_1COCl$.

In the first synthesis route, represented by reaction scheme (A), the first stage consists of reacting an acid chloride ($R_1COCl$) with 1,8-dihydroxyanthrone or anthralin (1) in the presence of a base such as pyridine, in an organic solvent such as toluene under a nitrogen atmosphere, with light and air excluded.

The second stage consists of treating the 1,8-dihydroxy-10-acylanthrone (2) by an acid anhydride of formula ($R_2CO)_2O$ either alone or mixed in an organic solvent such as toluene, or by an acid chloride $R_2COCl$ if the corresponding anhydride is not readily available.

To favor formation of the 10-monoacyl derivative (2), it is necessary to use excess acid chloride relative to anthralin, this excess being around 1.5 to 3 equivalents.

Moreover, it is recommended that the pyridine and acid chloride be added in two batches in order to limit formation of diacyl or triacyl products and to stop the reaction when the anthralin subjected to reaction has been transformed to the expected 10-monoacyl product.

The basic agent, such as pyridine, must also be used in excess relative to anthralin, and an excess of 1.8 to 3.2 equivalents has proved particularly desirable.

After addition of the first batch of pyridine and acid chloride, the temperature is raised to around 80°–90° C. for 30 minutes to 2 hours then, after cooling to room temperature, the supplementary quantity of pyridine is added to the reaction mixture, followed by the rest of the acid chloride. The temperature is again raised to around 80°–90° C. for 1 to 2 hours until complete disappearance of the anthralin.

After cooling, the pyridinium hydrochloride formed is eliminated by filtration or by extraction with water, and the toluene phase is concentrated to around 1/5 of its initial volume. The expected product is then purified by chromatography on a column of silica gel.

The 1,8-dihydroxy-10-acylanthrones (2) are generally eluted in the first fractions. Thereafter, by means of a solvent or a solvent mixture of increasing polarity, the mono-, di- and triacyloxy 10-acyl derivatives which may have been formed in the reaction are eluted.

In certain cases the 10-monoacyl derivative can be isolated by recrystallization without the need for chromatography.

In the second stage, in which organic solvent is not used, the reaction temperature is generally adjusted to between 100° and 150° C., and heating is stopped when complete disappearance of the starting material is indicated by thin-layer chromatography.

If an acid anhydride having a high boiling point and thus being difficult to eliminate by evaporation under vacuum is used, the reaction is preferably carried out in the presence of a solvent such as toluene.

The reaction is then performed at the boiling point of the organic solvent for 1 to 5 hours, until total disappearance of the starting material as indicated by thin-layer chromatography.

Generally speaking, the quantity of acid anhydride or acid chloride is in excess relative to the 1,8-dihydroxy-10-acylanthrone (2), this excess being at least 5 equivalents.

On completion of the reaction, the reaction mixture is poured into water and washed several times, particularly by means of sodium bicarbonate. The toluene phase is then dried over magnesium sulfate and filtered.

When an acid anhydride such as acetic anhydride is used, it can be eliminated by evaporation under vacuum.

The expected product is then purified either by recrystallization or by chromatography on silica gel, preferably using toluene or a mixture of toluene and ethyl acetate as the mobile phase.

In the second synthesis route, represented by reaction scheme (B), the first stage consists of preparing a 1,8-diacyloxyanthrone (3) by reacting 1,8-dihydroxyanthrone (1) with an excess of acid anhydride ($R_2CO)_2O$ or acid chloride $R_2COCl$, preferably severely hindered and without a hydrogen atom in the α-position with respect to the carbonyl group.

When an acid anhydride is used, the reaction conditions are not significantly different from those described above for the preparation of compounds of formula (I) from the monoacyl derivative (2).

When an acid chloride is used, it is employed in an excess of 2 to 5 equivalents with an equimolar quantity of pyridine, thus permitting good yields to be obtained and the reaction time to be shortened.

In a second stage, the carbanion of compound (3) is first prepared by treating compound (3) in an aromatic solvent or ether, preferably toluene or tetrahydrofuran, by one equivalent of a strong base such as sodium hydride, at a temperature between −70° C. and 25° C., preferably at 0° C.

The formation of the carbanion is extremely rapid (a few minutes) and is accompanied by the development of an intense blood-red color. When the evolution of hydrogen ceases, the acid chloride ($R_1COCl$) is added at a temperature between 0° and 30° C. The reaction is rapid and leads to the 1,8-diacyloxy-10-acylanthrone (I), which is then purified by the same methods as described above for the first synthesis method.

The present invention also relates to the use of compounds of formula (I) in human or veterinary medicine and in cosmetics.

In human or veterinary therapeutics, the compounds of the invention are powerful anti-proliferative agents, particularly in the treatment of psoriasis and warts, and excellent anti-inflammatory agents, particularly in the treatment of rheumatic diseases and of dermatoses such as eczema.

In cosmetics, the compounds of the invention can be used in the treatment of acne, dandruff, seborrhea and hair loss.

The cosmetic or pharmaceutical compositions can be prepared, for example, by adding the active compound of formula (I) in a concentration between 0.1 and 5% to various solid or liquid, nontoxic, inert supports generally used in compositions for cosmetic or therapeutic applications.

The pharmaceutical compositions can be administered by enteral, parenteral or topical procedures. For enteral administration, the compositions are made up in the form of tablets, powders, granules, capsules, pills, syrups, suspensions or solutions.

Of course the dosage is a function of the method of administration and of the intended activity.

The pharmaceutical compositions can also contain inert or possibly pharmacodynamically active additives. The tablets or granules, for example, can contain binders, fillers, supports or diluents.

The liquid compositions can be made up, for example, in the form of a water-miscible sterile solution. In addition to the active compound, the capsules can contain a filler or a thickener. The pharmaceuticals for oral administration can also contain agents for improving the taste as well as substances customarily used as preservers, stabilizers, regulators and emulsifiers. Salts and buffers can also be added.

The supports and diluents such as listed above can consist of organic or inorganic substances, for example, gelatin, lactose, starch, magnesium stearate, talc, gum arabic, vegetable and mineral oils, fillers, thickeners, dyes, humectants or polyalkylene glycols. When the pharmaceutical compositions are intended for topical application, they are made up in the form of an ointment, a salve, a tincture, a cream, a solution, a lotion, a micronized powder, a spray, a suspension or a shampoo.

The ointments or salves are preferred and are prepared by mixing the active compound of the invention with nontoxic inert supports which are appropriate for topical treatment.

For the purposes of illustration, and without limiting character, several examples of preparation of compounds in accordance with the invention as well as several examples of compositions for therapeutic and cosmetic application will be presented in the following:

EXAMPLE 1

Preparation of 1,8-diacetoxy-10-acetylanthrone (a) 1,8-Dihydroxy-10-acetylanthrone To a solution of 56.5 g (0.25 mol) of purified anthralin in 1750 cm$^3$ of anhydrous toluene being stirred at room temperature, 27.3 cm$^3$ (0.34 mol) of anhydrous pyridine was added first and then 21.4 cm$^3$ (0.3 mol) of acetyl chloride was added dropwise by means of a dropping funnel. Slight heating occurred during addition then, after the end of addition, the mixture was heated to a temperature of around 90° C. for 1 hour. The mixture was cooled and 27.3 cm$^3$ of pyridine and then, dropwise, 21.4 cm$^3$ of acetyl chloride were again added at 30°-35° C. The mixture was then stirred for 1 hour at 85°-90° C. After a check to insure that the anthralin had been transformed to the 10-acetyl derivative, the reaction mixture was cooled to room temperature then washed 3 times with water (250 cm$^3$). The toluene phase was decanted, dried over sodium sulfate and then concentrated to around 300 cm$^3$. The solution was then deposited on a column of silica gel and eluted with toluene and a 1:1 mixture of toluene and methylene chloride. The first fractions were combined and then concentrated under vacuum. The solid obtained was then recrystallized from toluene to yield 21 g of bright-yellow crystals of 1,8-dihydroxy-10-acetylanthrone having a melting point of 146° C.

Analysis: $C_{16}H_{12}O_4$ Calc.: C 71.63, H 4.51, O 23.85; Found: C 71.44, H 4.34, O 23.97.

(b) 1,8-Diacetoxy-10-acetylanthrone

A solution of 37.5 g of 1,8-dihydroxy-10-acetylanthrone obtained above in 350 cm$^3$ acetic anhydride was refluxed for 2 hours. The acetic acid and the excess anhydride were then eliminated by evaporation under reduced pressure. The crystalline product obtained was then washed with hexane, dissolved in methylene chloride and deposited on a column of silica gel. After elution by methylene chloride then by a 9:1 mixture of methylene chloride and ethyl acetate, followed by evaporation of the mobile phase, 29 g of white crystals having a melting point of 169° C. was obtained.

Analysis: $C_{20}H_{16}O_6$ Calc.: C 68.18, H 4.57, O 27.24; Found: C 68.23, H 4.66, O 27.06.

EXAMPLE 2

Preparation of 1,8-diacetoxy-10-propionylanthrone (a) 1,8-Dihydroxy-10-propionylanthrone To a suspension of 56.6 g (0.25 mol) of purified anthralin in 1750 m$^3$ of anhydrous toluene at room temperature, 27.3 cm$^3$ (0.34 mol) of anhydrous pyridine was added first and then 26.2 cm$^3$ (0.3 mol) of propionyl chloride was added dropwise in around 20 minutes. The mixture was then heated to around 85° C. for 1 hour. The mixture was recooled to room temperature, 27.3 cm$^3$ of pyridine and 26.2 cm$^3$ of propionyl chloride were again added and the mixture was heated for 1 hour to a temperature of around 85° C.

The precipitated pyridinium hydrochloride was filtered then washed with toluene. The toluene filtrates were then concentrated to around 1 liter then washed and dried over magnesium sulfate. The product was then fractionated by chromatography on silica gel, using first the hexane-toluene mixture and then toluene as the mobile phase.

After evaporation of the different fractions, those containing the 1,8-dihydroxy-10-propionylanthrone were combined and dissolved at room temperature in toluene. By addition of hexane the expected product was precipitated and was isolated by sucking off the solvents.

The product was then dried and 54.6 g of pale-yellow crystals of 1,8-dihydroxy-10-propionylanthrone having a melting point of 154° C. was obtained.

Analysis: $C_{17}H_{14}O_4$ Calc.: C 72.33, H 4.99; Found: C 72.14, H 5.06.

(b) 1,8-Diacetoxy-10-propionylanthrone

A solution of 4 g of 1,8-dihydroxy-10-propionylanthrone obtained above in 60 cm³ of toluene and a few crystals of p-toluenesulfonic acid was prepared and 6.7 cm³ (5 equivalents) of acetic anhydride was added. The mixture was then refluxed for 10 hours. After being cooled, the mixture was washed with water and the toluene phase was dried over sodium sulfate. After concentration and cooling, the 1,8-diacetoxy-10-propionylanthrone crystallized out. The solvent was sucked off and the product was dried to yield 2.5 g of white crystals with a melting point of 162° C.

Analysis: $C_{21}H_{18}O_6$ Calc: C 68.84, H 4.95, O 26.20; Found: C 68.71, H 4.93, O 26.16.

EXAMPLE 3

Preparation of 1,8-diisobutyryloxy-10-propionylanthrone

A solution of a few crystals of p-toluenesulfonic acid in 30 cm³ of toluene was brought to reflux in a 50-cm³ three-necked flask equipped with a condenser and a dropping funnel.

Thereafter 4 g of 1,8-dihydroxy-10-propionylanthrone obtained as in Example 2(a) was introduced then 12 cm³ (5 equivalents) of isobutyric anhydride was added.

The mixture was then refluxed for 14 hours, which was the time necessary for disappearance of the starting material. The reaction mixture was then cooled to room temperature and washed with water and sodium bicarbonate. The toluene phase was dried over sodium sulfate and then concentrated by means of a rotary evaporator. The 1,8-diisobutyryloxy-10-propionylanthrone was precipated by addition of hexane. After removal of the solvent by suction and recrystallization from a toluene-hexane mixture, 1.8 g of beige crystals with a melting point of 122°–123° C. was obtained.

Analysis: $C_{25}H_{26}O_6$ Calc.: C 71.07, H 6.20, O 22.72; Found: C 71.11, H 6.24, O 22.57.

EXAMPLE 4

Preparation of 1,8-dipropionyloxy-10-isobutyrylanthrone (a) 1,8-Dihydroxy-10-isobutyrylanthrone To a solution of 56.6 g (0.25 mol) of anthralin in 1750 cm³ of absolute toluene and 27.3 cm³ of pyridine, 31.5 cm³ (0.3 mol) of isobutyryl chloride was added with stirring over 30 minutes at room temperature.

The reaction mixture was then heated to 85° C. for 1 hour. After this mixture had recooled to room temperature, 27.3 cm³ of pyridine and 31.5 cm³ of isobutyryl chloride were again added. The suspension obtained was then heated to 85°–90° C. for 1 hour.

The precipitated pyridinium hydrochloride was eliminated by filtration then washed with toluene. The toluene filtrates were concentrated to around 500 cm³ under reduced pressure, washed several times with water then dried over magnesium sulfate.

The product was then fractionated by chromatography on silica gel, using toluene and then a mixture of toluene and ethyl acetate as the mobile phase. The different fractions containing the 1,8-dihydroxy-10-isobutyrylanthrone were then concentrated and recrystallized from a toluene-hexane mixture.

In this way 25 g of yellow crystals of 1,8-dihydroxy-10-isobutyrylanthrone having a melting point of 160° C. was obtained.

Analysis: $C_{18}H_{16}O_4$ Calc.: C 72.97, H 5.44, O 21.59; Found: C 73.00, H 5.42, O 21.77.

After further chromatographic fractionation on silica gel of the later fractions in toluene, followed by evaporation and recrystallization from a toluene-hexane mixture, 12 g of light-beige crystals having a melting point of 153° C. was isolated. The analysis of this product corresponded to 1,8-diisobutyryloxy-10-isobutyrylanthrone.

Analysis: $C_{26}H_{28}O_6$ Calc.: C 71.35; H 6.40, O 21.95; Found: C 71.10, H 6.42, O 21.99.

(b) 1,8-Dipropionyloxy-10-isobutyrylanthrone

Using the same procedure as that described in Example 3, 2 g of 1,8-dihydroxy-10-isobutyrylanthrone obtained above was refluxed in toluene with 5 equivalents of propionic anhydride.

On completion of the reaction, the toluene phase was washed successively with water and sodium bicarbonate solution and was then dried.

By addition of hexane to the toluene phase, a precipitate was formed. The solvents were sucked off and the precipitate was dried. The yield was 1.1 g of white crystals with a melting point of 119° C.

Analysis: $C_{24}H_{24}O_6$ Calc.: C 70.57, H 5.92, O 23.50; Found: C 70.59; H 5.96, O 23.57.

EXAMPLE 5

Preparation of 1,8-diacetoxy-10-isopentanoylanthrone (a) 1,8-Dihydroxy-10-isopentanoylanthrone The same procedure as that described in Example 4(a) was used, except that the isobutyryl chloride was replaced by the corresponding quantity of isopentanoyl chloride.

After chromatography on silica gel, evaporation of the solvent and recrystallization from a toluene-hexane mixture, 22 g of yellow crystals of 1,8-dihydroxy-10-isopentanoylanthrone with a melting point of 141° C. was obtained.

Analysis: $C_{19}H_{18}O_4$ Calc.: C 73.53, H 5.84, O 20.62; Found: C 73.34, H 5.89, O 20.48.

After evaporation of the filtrates and further chromatography on silica gel with toluene as the mobile phase, followed by evaporation, light-beige crystals with a melting point of 109° C. were obtained. The analysis of this product corresponded to 1,8-diisopentanoyloxy-10-isopentanoylanthrone.

Analysis: $C_{29}H_{34}O_6$ Calc.: C 72.78, H 7.16, O 20.06; Found: C 72.06, H 7.18, O 19.92.

(b) 1,8-Diacetoxy-10-isopentanoylanthrone

Using the same procedure as that described in Example 3, 5 g of 1,8-dihydroxy-10-isopentanoylanthrone obtained above was treated with 5 equivalents of acetic anhydride in 50 cm³ of anhydrous toluene in the presence of a trace of p-toluenesulfonic acid.

On completion of the reaction, the mixture was washed with water and the toluene phase was separated, dried over sodium sulfate then concentrated under vacuum. The solid obtained was then dissolved in methylene chloride and fractionated by chromatography on silica gel.

After elution with a 9:1 mixture of toluene and ethyl acetate and evaporation of the mobile phase, 4 g of pale-yellow crystals with a melting point of 136° C. was obtained.

Analysis: $C_{23}H_{22}O_6$ Calc.: C 70.04, H 5.62, O 24.34; Found: C 70.30, H 5.70, O 24.34.

EXAMPLE 6

Preparation of 1,8-dipropionyloxy-10-propionylanthrone

Using the same procedure as that described in Example 3, 5 g of 1,8-dihydroxy-10-propionylanthrone obtained in Example 2(a) was treated with 5 equivalents of propionic anhydride. The product was then fractionated by chromatography on a column of silica gel, using a 9:1 mixture of toluene and ethyl acetate as the mobile phase. Evaporation and then recrystallization from toluene led to 1.5 g of beige crystals with a melting point of 125° C.

Analysis: $C_{23}H_{22}O_6$ Calc.: C 70.04, H 5.62, O 24.34; Found: C 69.92, H 5.50, O 24.10.

EXAMPLE 7

Preparation of 1,8-dipropionyloxy-10-isopentanoylanthrone

Using the same procedure as that described in Example 3, 6 g of 1,8-dihydroxy-10-isopentanoylanthrone obtained in Example 5(a) was treated with 5 equivalents of propionic anhydride. After 4 hours of reflux, it was demonstrated by thin-layer chromatography that the starting material had disappeared. The reduction mixture was cooled to room temperature, whereupon the expected product crystallized out. The solvents were sucked off and the product was recrystallized twice from a toluene-hexane mixture.

The yield was 2.1 g of beige crystals with a melting point of 124° C.

Analysis: $C_{25}H_{26}O_6$ Calc.: C 71.07, H 6.20, O 22.72; Found: C 71.11, H 6.22, O 22.89.

EXAMPLE 8

Preparation of 1,8-diacetoxy-10-cyclopentylcarbonylanthrone (a) 1,8-Dihydroxy-10-cyclopentylcarbonylanthrone This compound was obtained by using the same procedure as that described in Example 4(a), except that the isobutyryl chloride was replaced by the corresponding quantity of cyclopentanecarboxylic acid chloride.

After chromatography on silica gel, evaporation of the solvent and crystallization in hexane, 24 g of a yellow powder of 1,8-dihydroxy-10-cyclopentylcarbonylanthrone with a melting point of 164° C. was obtained.

Analysis: $C_{20}H_{18}O_4$ Calc.: C 74.52, H 5.63, O 19.85; Found: C 74.38, H 5.75, O 19.66.

(b) 1,8-Diacetoxy-10-cyclopentylcarbonylanthrone

A solution of 9 g of 1,8-dihydroxy-10-cyclopentylcarbonylanthrone obtained above in 150 cm³ of acetic anhydride was heated with stirring to a temperature between 130° and 140° C. for 3 hours. The solution was then concentrated under reduced pressure in a rotary evaporator.

The liquid residue was then treated with hexane, thus causing precipitation of the expected product. The solvents were sucked off from this product under vacuum. Thereafter the solid was dissolved in methylene chloride and fractionated by chromatography on a column of silica gel. After concentration of the eluted methylene chloride phases and recrystallization from a toluene-hexane mixture, 4.2 g of 1,8-diacetoxy-10-cyclopentylcarbonylanthrone was obtained in the form of pale-yellow crystals having a melting point of 180° C.

Analysis: $C_{24}H_{22}O_6$ Calc.: C 70.92, H 5.46, O 23.62; Found: C 71.01, H 5.47, O 23.76.

EXAMPLE 9

Preparation of 1,8-diacetoxy-10-cyclohexylcarbonylanthrone (a) 1,8-Dihydroxy-10-cyclohexylcarbonylanthrone This compound was obtained by using the same procedure as that described in Example 4(a), except that the isobutyryl chloride was replaced by the corresponding quantity of cyclohexanecarboxylic acid chloride.

After chromatography on silica gel and crystallization in a hexane-toluene mixture, 1.8 g of yellow crystals of 1,8-dihydroxy-10-cyclohexylcarbonylanthrone having a melting point of 220° C. was obtained.

Analysis: $C_{21}H_{10}O_4$ Calc.: C 74.98, H 5.99, O 19.03; Found: C 74.78, H 5.91, O 19.22.

By evaporation of the later fractions eluted with a 9:1 mixture of toluene and ethyl acetate, 5 g of clear-yellow crystals with a melting point of 158° C. was isolated. The analysis of this product corresponded to 1,8-dicyclohexylcarbonyloxy-10-cyclohexylcarbonylanthrone.

Analysis: $C_{35}H_{40}O_6$ Calc.: C 75.51, H 7.24, O 17.25; Found: C 75.48, H 7.37, O 16.97.

(b) 1,8-Diacetoxy-10-cyclohexylcarbonylanthrone

This compound was obtained by using the same procedure as that described in Example 8(b), by treating 9 g of 1,8-dihydroxy-10-cyclohexylcarbonylanthrone with 150 cm³ of acetic anhydride. After 3 hours the mixture was concentrated, and the oil obtained crystallized out by agitation in hexane. After the solvents had been sucked off, the 11 g of product obtained was dissolved in 150 cm³ of toluene heated to 100° C. and stirred in the presence of 10 g of silica gel. After a few minutes, the solution was filtered and the filtrate was cooled to 0° C. In this way 6 g of light-beige crystals of 1,8-diacetoxy-10-cyclohexylcarbonylanthrone having a melting point of 188° C. was obtained.

Analysis: $C_{25}H_{24}O_6$ Calc.: C 71.41, H 5.75, O 22.83; Found: C 71.58, H 5.71, O 22.68.

EXAMPLE 10

Preparation of 1,8-dipivaloyloxy-10-propionylanthrone

To a solution of 5 g of 1,8-dihydroxy-10-propionylanthrone obtained according to Example 2(a) in 100 cm³ of anhydrous toluene, 5.7 cm³ (4 molar equivalents) of anhydrous pyridine and 8.7 cm³ (4 molar equivalents) of pivaloyl chloride were added. The mixture was then heated to 100° C. for 8 hours, after which the greater part of the starting material had been transformed. Thereafter 100 cm³ of water was added at room temperature, the mixture was decanted and the organic phase was washed with water, dried over sodium sulfate and concentrated. The oily residue obtained was dissolved in methylene chloride and deposited on a column of silica gel. Chromatographic fractionation was then performed using a 15:3:2 mixture of toluene, methylene chloride and ethyl acetate as the mobile phase. After concentration of the eluted phases and recrystallization from pentane, 2 g of pale-yellow crystals of 1,8-dipivaloyloxy-10-propionylanthrone having a melting point of 115° C. was obtained.

Analysis: $C_{27}H_{30}O_6$ Calc.: C 71.98, H 6.71, O 21.31; Found: C 71.88, H 6.75, O 21.50.

EXAMPLE 11

Preparation of 1,8-dipivaloyloxy-10-benzoylanthrone (a) 1,8-Dipivaloyloxyanthrone A solution of 90 g (0.4 mol) of 1,8-dihydroxyanthrone and 130 cm$^3$ (4 equivalents) of pyridine in 1 liter of anhydrous toluene was prepared in a 2-liter reactor.

The mixture was heated to a temperature of 90°–100° C. with stirring, and then 197 cm$^3$ (4 equivalents) of pivaloyl chloride was added dropwise. On completion of the introduction of pivaloyl chloride, the reaction mixture was refluxed for 4 hours.

After filtration of the reaction mixture at room temperature, the filtrate was washed with aqueous bicarbonate solution and then with water to neutral pH. Thereafter the organic phase was dried over sodium sulfate and then concentrated in the rotary evaporator under reduced pressure. The solid obtained was then stirred in 300 cm$^3$ of hexane, after which the solvent was sucked off and the solid was dried. The product was 110 g of a yellow solid which, after recrystallization from ethyl acetate, yielded light-yellow needles having a melting point of 174° C.

Analysis Calc.: C 72.70, H 6.61, O 20.18; Found: C 72.73, H 6.61, O 20.40.

(b) 1,8-Dipivaloyloxy-10-benzoylanthrone

To a solution of 5 g of 1,8-dipivaloyloxyanthrone obtained above in 50 cm$^3$ of anhydrous tetrahydrofuran, 1.1 molar equivalents of sodium hydride was added with stirring and with exclusion of light and atmospheric humidity. The color of the reaction mixture then changed to blood-red. When the evolution of hydrogen had ceased, 1.1 equivalents of benzoyl chloride was introduced dropwise at 0° C. Thereafter the reaction mixture was stirred for 2 hours at room temperature, after which 5 cm$^3$ of acetic acid was added and the mixture was poured into 300 cm$^3$ of water. The liquids were sucked from the resulting precipitate, which was then dried and dissolved in 40 cm$^3$ of methylene chloride. After filtration, 250 cm$^3$ of hexane was added to the filtrate, and the solvents were sucked from the white product formed. After dissolution in the minimum volume of methylene chloride and progressive addition of hexane, 1,8-dipivaloyloxy-10-benzoylanthrone crystallized out. The solvent was sucked from this product, which was then dried to yield 3.5 g of white crystals having a melting point of 191° C.

Analysis: C$_{31}$H$_{30}$O$_6$ Calc.: C 74.68, H 6.06, O 19.25; Found: C 74.85, H 6.07, O 19.50.

EXAMPLE 12

Preparation of 1,8-dipivaloyloxy-10-(2'-thenoyl)-anthrone

The same procedure as that described in Example 11(b) was used to prepare a solution of the carbanion of 1,8-dipivaloyloxyanthrone from 5 g of starting material, and 1.1 equivalents of theonyl chloride was added at 0° C. Thereafter the mixture was stirred for 2 hours at room temperature, and 5 cm$^3$ of acetic acid was added. The solution was concentrated under reduced pressure, diluted with 200 cm$^3$ of methylene chloride and washed with water. The organic phase was decanted, dried over magnesium sulfate, concentrated and deposited on a column of silica gel. The expected product was eluted first with a 1:1 mixture of toluene and methylene chloride and then with methylene chloride. After concentration of the eluted phases, the solid obtained was dissolved in the minimum volume of toluene. The toluene phase was filtered and then poured into hexane.

After crystallization of the 1,8-dipivaloyloxy-10-(2'thenoyl)anthrone, the solvents were sucked from it and it was dried. In this way 1.5 g of pale-yellow crystals having a melting point of 210° C. was obtained.

Analysis: C$_{29}$H$_{28}$O$_6$S Calc.: C 69.03, H 5.59, O 19.03, S 6.35; Found: C 69.05, H 5.62, O 19.05, S 6.20.

EXAMPLE 13

Preparation of 1,8-dipivaloyloxy-10-butyrylanthrone (a) 1,8-Dihydroxy-10-butyrylanthrone To a stirred suspension of 51 g (0.22 mol) of 1,8-dihydroxyanthrone in 1.5 liters of toluene, kept under an inert atmosphere and shielded from light, 23.8 cm$^3$ of pyridine was first added all at once and then 27.4 cm$^3$ of butyryl chloride was added dropwise over 15 minutes. The mixture was then heated to a temperature of 80°–90° C. for 1 hour. Subsequently, the same quantities as before of pyridine and butyryl chloride (i.e., a total of 2.7 molar equivalents for pyridine and of 2.4 molar equivalents for the acid chloride) were added at room temperature.

The reaction mixture was then reheated to 80°–90° C. for 1 hour. After being cooled to room temperature, the mixture was poured into 500 cm$^3$ of acidulated water. The organic phase was decanted, washed with water until the washings became neutral and dried over magnesium sulfate. This phase was then fractionated by chromatography on a silica gel column, using toluene as the mobile phase. The eluted phases were concentrated and poured into hexane, thus causing crystallization of 1,8-dihydroxy-10-butyrylanthrone. The solvent was sucked from this product, which was then dried to yield 20 g of yellow crystals having a melting point of 138° C.

Analysis: C$_{18}$H$_{16}$O$_4$ Calc.: C 72.96, H 5.44, O 21.60; Found: C 72.75, H 5.48, O 21.38.

(b) 1,8-Dipivaloyloxy-10-anthrone

To a stirred solution of 5 g of 1,8-dihydroxy-10-butyrylanthrone obtained above in 150 cm$^3$ of toluene, shielded from light and kept under an inert atmosphere, 5.5 cm$^3$ of pyridine and then 8.4 cm$^3$ of pivaloyl chloride (4 molar equivalents) were added. The reaction mixture was then maintained under toluene reflux for 15 hr.

The pyridinium hydrochloride formed was filtered at room temperature, and the filtrate was concentrated under reduced pressure. Thereafter the product obtained was dissolved in 400 cm$^3$ of dichloromethane and the solution obtained was washed with acidulated water and then with water until the washings reached a neutral pH. The organic phase was decanted, dried over magnesium sulfate and concentrated. The product was then precipitated by addition of 100 cm$^3$ of hexane. After the solvent had been sucked off and the product dissolved in the minimum volume of hot toluene, the toluene phase was filtered rapidly and then poured into 100 cm$^3$ of hexane. By cooling to 0° C., the precipitated product was obtained in the form of pale-yellow crystals. The solvents were sucked from this product, which was then dried to yield 5 g of 1,8-dipivaloyloxy-10-butyrylanthrone having a melting point of 120° C.

Analysis: Calc.: C 72.39, H 6.94, O 20.67; Found: C 72.41, H 7.06, O 20.71.

EXAMPLE 14

Preparation of 1,8-diisobutyryloxy-10-cyclohexylcarbonylanthrone

A stirred solution of 5 g of 1,8-dihydroxy-10-cyclohexylcarbonylanthrone obtained in Example 9(a) in 50 cm$^3$ of isobutyric anhydride, shielded from light and kept under an inert atmosphere, was heated to a temperature of 110° C. for three hours. The excess isobutyric anhydride and the isobutyric acid formed during the reaction were eliminated by evaporation under vacuum. The raw product crystallized out on cooling. This product was dissolved in the minimum volume of toluene, and the solution was deposited on a silica gel chromatographic column (mobile phase: toluene). The later fractions were evaporated to yield 4 g of a product which was then dissolved in the minimum volume of toluene. After filtration, the expected product was crystallized by addition of hexane. The solvents were sucked from the crystals, which were then dried. The yield was 3.3 g of 1,8-diisobutyryloxy-10-cyclohexylcarbonylanthrone in the form of yellow crystals with a melting point of 129° C.

The infrared and $^1$H-N.M.R. spectra corresponded to the expected structure.

Analysis: $C_{28}H_{32}O_6$ Calc.: C 72.39, H 6.94, O 20.66; Found: C 72.41, H 6.97, O 20.55.

EXAMPLE 15

Preparation of 1,8-dibenzoyloxy-10-propionylanthrone

To a stirred solution containing 10 g of 1,8-dihydroxy-10-propionylanthrone obtained in Example 2(a) as well as 8.1 cm$^3$ (2 equivalents) of benzoyl chloride, kept at room temperature and under an inert atmosphere, 2 equivalents of triethylamine was added slowly.

The reaction mixture became very brown, and stirring was continued for another two hours. The mixture was then washed twice with water. The organic solution was dried over magnesium sulfate, concentrated and deposited directly on a column of silica gel. This solution was eluted first with toluene, then with a mixture of toluene and methylene chloride and finally with a mixture of methylene chloride and ethyl acetate.

After evaporation of the mobile phase, 6 g of unreacted 1,8-dihydroxy-10-propionylanthrone was isolated from the first fractions and 7.5 g of 1,8-dibenzoyloxy-10-propionylanthrone was isolated from the later fractions. This 1,8-dibenzoyloxy-10-propionylanthrone was recrystallized from toluene to yield 5.1 g of very light-beige crystals having a melting point of 160° C. The infrared and $^1$H-N.M.R. spectra corresponded to the expected structure.

Analysis: $C_{31}H_{22}O_6$ Calc.: C 75.91, H 4.52, O 19.57; Found: C 75.70, H 4.54, O 19.37.

EXAMPLES OF PHARMACEUTICAL AND COSMETIC COMPOSITIONS

Example 1

Insoluble 0.5-g tablet 1,8-Diacetoxy-10-acetylanthrone: 0.100 g,
Lactose: 0.082 g,
Stearic acid: 0.003 g,
Purified talc: 0.015 g,
Sweetener, q.s.
Dye, q.s.
Rice starch, q.s.: 0.500 g.

This tablet is obtained by direct dry compression of the mixture of the different constituents.

EXAMPLE 2

Insoluble 0.8-g tablet 1,8-Diacetoxy-10-propionylanthrone: 0.200 g,
Lactose: 0.200 g,
20% Aqueous gum arabic: 0.080 g,
Liquid paraffin: 0.004 g,
Purified talc: 0.016 g,
Starch, q.s.ad: 0.800 g.

This tablet is obtained by wet granulation of the mixture of 1,8-diacetoxy-10-propionylanthrone, starch, lactose and 20% aqueous gum arabic. The granulate is dried and then screened. The product is mixed with the paraffin and the talc. The total mixture is then compressed. In this example, 1,8-diacetoxy-10-propionylanthrone can be replaced by 1,8-diacetoxy-10-isopentanoylanthrone.

EXAMPLE 3

Granules in 3-g bags 1,8-Diisobutyryloxy-10-isobutyrylanthrone: 0.150 g,
Saccharose: 2.220 g,
Methylcellulose: 0.030 g,
Purified water: 0.600 g.

The paste obtained by mixing the four constituents is granulated by the wet process and then dried.

In this example, the 1,8-diisobutyryloxy-10-isobutyrylanthrone can be replaced by 1,8-diisopentanoyloxy-10-isopentanoylanthrone.

EXAMPLE 4

1-g Capsules containing 0.5 g of active compound

Capsule contents: oil-base suspension
1,8-Dicyclohexylcarbonyloxy-10-cyclohexylcarbonylanthrone: 0.050 g,
Cod-liver oil, q.s.ad: 0.500 g.

The envelope of the capsule is made by molding and then drying an appropriate mixture consisting of gelatin, glycerin, water and preservative. The suspension is introduced into the capsule, which is then sealed.

EXAMPLE 5

Capsule containing 0.3 g of powder

Composition of the powder:
1,8-Dipropionyloxy-10-isobutyrylanthrone: 0.080 g,
Corn starch: 0.060 g,
Lactose, q.s.ad: 0.300 g.

The powder is packed in a capsule consisting of gelatin, titanium dioxide and preservative.

In this example, 1,8-dipropionyloxy-10-isobutyrylanthrone can be replaced by 1,8-diisobutyryloxy-10-propionylanthrone.

EXAMPLE 6

Potable suspension in tinted 10-ml phials 1,8-Diacetoxy-10-cyclopentylcarbonylanthrone: 0.120 g,
Peanut oil, q.s.ad: 10 ml.
This phial must be shaken before use.

EXAMPLE 7

32-mg hypodermic tablet

Micronized 1,8-diacetoxy-10-acetylanthrone: 0.005 g,
Sodium chloride: 0.027 g.

The mixture is granulated by means of a solution of polyethyleneglycol 4000 in acetone, and is then dried and compressed. The tablet is mixed extemporaneously with 3 ml of water to form an injectable preparation.

In this example, 1,8-diacetoxy-10-acetylanthrone can be replaced by 1,8-diacetoxy-10-propionylanthrone, by 1,8-diacetoxy-10-cyclopentylcarbonylanthrone or by 1,8-diacetoxy-10-cyclohexylcarbonylanthrone.

EXAMPLE 8

1-ml Phials of oil-base suspension suitable for intramuscular injection 1,8-Diisobutyryloxy-10-isobutyrylanthrone: 0.0001 g,
Cod-liver oil: 1 ml.

In this example, 1,8-diisobutyryloxy-10-isobutyrylanthrone can be replaced by 1,8-dipropionyloxy-10-isobutyrylanthrone or by 1,8-dicyclohexylcarbonyloxy-10-cyclohexylcarbonylanthrone.

EXAMPLE 9

Hydrophobic ointment 1,8-Diacetoxy-10-acetylanthrone: 1.00 g,
Petrolatum: 49.00 g,
Ceresin: 15.00 g,
Paraffin oil: 35.00 g.

In this example, 1,8-diacetoxy-10-acetylanthrone can be replaced by 1,8-dipropionyloxy-10-isobutyrylanthrone.

EXAMPLE 10

Ointment 1,8-Diisobutyryloxy-10-isobutyrylanthrone: 5.00 g,
Anhydrous Eucerin (mixture of emulsive lanolin alcohols, waxes and hydrocarbon-base oils) sold by the BDF Company: 60.00 g,
Microcrystalline wax: 15.00 g,
Paraffin oil, q.s.ad: 100.00 g.

In this example, 1,8-diisobutyryloxy-10-isobutyrylanthrone can be replaced by 1,8-diisopentanoyloxy-10-isopentanoylanthrone.

EXAMPLE 11

Nonionic emulsion for topical application 1,8-Diacetoxy-10-isopentanoylanthrone: 0.70 g,
Anhydrous Eucerin: 70.00 g,
Paraffin oil: 10.00 g,
Preservative, q.s.
Sterile demineralized water, q.s.ad: 100.00 g.

For good preservation, this emulsion will have to be stored away from the heat.

In this emulsion, 1,8-diacetoxy-10-isopentanoylanthrone can be replaced by 1,8-diacetoxy-10-propionylanthrone.

EXAMPLE 12

Nonionic emulsion 1,8-Diacetoxy-10-cyclopentylcarbonylanthrone: 1.00 g,
Arlacel 481 (unsaturated fatty acid ester of glycerol and of sorbitan) of the ATLAS Company: 15.00 g,
Paraffin oil: 65.00 g,
Preservatives, q.s.
Water, q.s.ad.: 100.00 g.

EXAMPLE 13

Anhydrous gel 1,8-Diisobutyryloxy-10-propionylanthrone: 1.50 g,
Aerosil 200 (silica) of the DEGUSSA Company: 7.00 g,
isopropyl myristate, q.s.ad: 100.00 g.

In this example, 1,8-diisobutyryloxy-10-propionylanthrone can be replaced by 1,8-diacetoxy-10-cyclopentylcarbonylanthrone.

EXAMPLE 14

Two-Part milk to be emulsified extemporaneously

1st part:
1,8-Diacetoxy-10-cyclohexylcarbonylanthrone: 2.00 g,
Miglycol 812 (triglycerides of capric and caprylic acids) of the DYNAMIT NOBEL Company, q.s.ad: 20.00 g.

2nd part:
Tween 80 (monooleate of polyoxyethylenated sorbitan containing 20 moles of ethylene oxide) of the ATLAS Company: 10.00 g,
Preservatives, q.s.
Sterile demineralzed water, q.s.ad: 80.00 g.

The first part is shaken to force the active compound into suspension, and the two parts are mixed before applying the milk.

EXAMPLE 15

Stick 1,8-Diisobutyryloxy-10-isobutyrylanthrone: 5.00 g,
Cocoa butter: 12.50 g,
Ozokerite: 18.50 g,
Refined white paraffin: 6.25 g,
Paraffin oil: 12.75 g,
Isopropyl myristate, q.s.ad: 100.00 g.

In this example, 1,8-diisobutyryloxy-10-isobutyrylanthrone can be replaced by 1,8-diacetoxy-10-propionylanthrone.

EXAMPLE 16

Anti-hair-loss and anti-dandruff hair-care composition 1,8-Dipivaloyloxy-10-butyrylanthrone: 0.50 g.
Salicylic acid: 0.10 g,
Benzyl salicylate, q.s.ad: 100.00 g.

This composition is applied to the scalp for 1.4 hour, after which a conventional shampoo is performed.

EXAMPLE 17

Anti-hair-loss and anti-dandruff hair-care composition 1,8-Dipropionyloxy-10-propionylanthrone: 0.50 g,
Stannous chloride: 0.30 g,
Isopropyl myristate, q.s.ad: 100.00 g.

This composition is applied to the scalp for ¼ hour, after which a conventional shampoo is performed.

EXAMPLE 18

Anti-acne composition in the form of cream

Magnesium lanolate: 3.40 g,
Lanolin alcohol: 2.80 g
Perhydrosqualene: 20.00 g,

Isopropyl myristate: 5.00 g,
Pure sesame oil: 10.00 g,
Paraffin oil: 8.80 g,
Salicylic acid: 1.00 g,
Methyl p-hydroxybenzoate: 0.30 g,
1,8-dipivaloyloxy-10-benzoylanthrone: 1.00 g,
Sterile demineralized water, q.s.ad: 100.00 g,

What is claimed is:

1. A compound of the formula

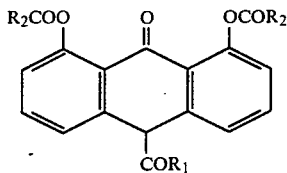 (I)

wherein $R_1$ and $R_2$ are the same or different and represent a straight-chain or branched alkyl group of 1 to 15 carbon atoms, a cycloalkyl group of 3 to 6 carbon atoms, a 2-furyl, 3-furyl, 3-pyridyl, 4-pyridyl or 2-thienyl group or an aromatic group of the formula

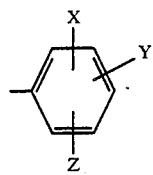

wherein X, Y and Z are the same or different and represent hydrogen, alkyl of 1 to 3 carbon atoms, trifluoromethyl, alkoxy with 1 to 4 carbon atoms, halogen, nitro or hydroxy groups.

2. Compound of claim 1 wherein the alkyl group is methyl, ethyl, propyl, isopropyl, butyl, isobutyl, tertiary butyl, pentyl, isopentyl, heptyl, nonyl, undecyl or pentadecyl.

3. Compound of claim 1 wherein the cycloalkyl group is cyclopentyl or cyclohexyl.

4. Compound of claim 1 wherein the aromatic group is phenyl or a mono- or disubstituted phenyl, wherein the radicals X, Y and Z represent hydrogen, methyl, ethyl, tertiary butyl, methoxy, ethoxy, chloro or fluoro.

5. A compound of claim 1 which is a member of the class consisting of
1,8-diacetoxy-10-acetylanthrone,
1,8-diacetoxy-10-propionylanthrone,
1,8-dipropionyloxy-10-propionylanthrone,
1,8-diisobutyryloxy-10-propionylanthrone,
1,8-diacetoxy-10-isobutyrylanthrone,
1,8-dipropionyloxy-10-isobutyrylanthrone,
1,8-diisobutyryloxy-10-isobutyrylanthrone,
1,8-dipivalyloxy-10-pivaloylanthrone,
1,8-diacetoxy-10-isopentanoylanthrone,
1,8-dipivaloyloxy-10-propionylanthrone,
1,8-dipropionyloxy-10-isopentanoylanthrone,
1,8-diisopentanoyloxy-10-isopentanoylanthrone,
1,8-dicyclohexylcarbonyloxy-10-cyclohexylcarbonylanthrone,
1,8-diacetoxy-10-cyclopentylcarbonylanthrone,
1,8-diacetoxy-10-cyclohexylcarbonylanthrone,
1,8-dipivaloyloxy-10-benzoylanthrone,
1,8-dipivaloyloxy-10-(2'-thenoyl)-anthrone,
1,8-dipivaloyloxy-10-butyrylanthrone.

6. Pharmaceutical composition for treatment of psoriasis, warts, rheumatism, dermatoses or eczema containing an effective dose of a compound of claim 1 and a pharmaceutically acceptable carrier.

7. Pharmaceutical composition of claim 6, wherein the concentration of the compound of claim 1 is between 0.1 and 5% by weight.

8. Cosmetic preparation for treatment of acne, dandruff, or seborrhea containing an effective dose of a compound of claim 1 and a cosmetically acceptable carrier.

* * * * *